United States Patent [19]

Le-Khac

[11] Patent Number: 4,892,533
[45] Date of Patent: Jan. 9, 1990

[54] ULTRAHIGH WATER-ABSORBING FIBER-FORMING COMPOSITION

[75] Inventor: Bi Le-Khac, West Chester, Pa.

[73] Assignee: Arco Chemical Technology, Inc., Wilmington, Del.

[21] Appl. No.: 228,634

[22] Filed: Aug. 4, 1988

Related U.S. Application Data

[62] Division of Ser. No. 834,075, Feb. 26, 1986, abandoned.

[51] Int. Cl.$^4$ ............................................. A61F 13/16
[52] U.S. Cl. ....................................... 604/368; 525/73; 524/916; 526/930
[58] Field of Search ................... 604/367–378; 524/108, 916; 523/111; 525/327.7, 73; 526/930; 8/DIG. 11, 120, 193

[56] References Cited

U.S. PATENT DOCUMENTS

| | | | |
|---|---|---|---|
| 2,601,254 | 7/1949 | Bruson | 524/108 |
| 2,734,040 | 2/1956 | Jones | 524/108 |
| 2,755,265 | 7/1956 | Riedeman | 524/108 |
| 2,811,533 | 10/1957 | Riedeman | 524/108 |
| 3,157,562 | 11/1964 | Kine et al. | 604/372 |
| 3,169,121 | 2/1965 | Goldberg | 524/108 |
| 3,299,184 | 1/1967 | Whitworth, Jr. | 525/327.6 |
| 3,578,623 | 5/1971 | Weissermel et al. | 524/108 |
| 3,669,103 | 6/1972 | Harper et al. | 128/156 |
| 3,670,731 | 6/1972 | Harmon | 604/372 |
| 3,678,016 | 7/1972 | Zimmerman et al. | 525/327.6 |
| 3,810,468 | 5/1974 | Harper | 604/368 |
| 3,901,236 | 8/1975 | Assarsson et al. | 604/368 |
| 3,936,441 | 2/1976 | Holst et al. | 604/372 |
| 3,954,721 | 5/1976 | Gross | 525/327.7 |
| 3,963,434 | 6/1976 | Ward et al. | 8/120 |
| 3,980,663 | 9/1976 | Gross | 524/389 |
| 3,983,095 | 9/1976 | Bashaw | 525/327.7 |
| 3,985,705 | 10/1976 | Georgoudis | 524/108 |
| 3,989,586 | 11/1976 | Bashaw | 162/168.4 |
| 3,993,616 | 11/1976 | Gross | 604/368 |
| 4,056,502 | 11/1977 | Gross | 523/111 |
| 4,062,817 | 12/1977 | Westerman | 523/111 |
| 4,111,922 | 9/1978 | Beede et al. | 523/111 |
| 4,155,893 | 5/1979 | Fujimoto et al. | 604/368 |
| 4,155,957 | 5/1979 | Sasayama | 260/897 B |
| 4,160,754 | 7/1979 | Shapel et al. | 524/916 |
| 4,171,308 | 10/1979 | Kaiya et al. | 524/108 |
| 4,175,068 | 11/1979 | Kaiya et al. | 524/108 |
| 4,190,562 | 2/1980 | Westerman | 523/111 |
| 4,211,851 | 7/1980 | Sasayama | 525/108 |
| 4,235,237 | 11/1980 | Mesek et al. | 604/372 |
| 4,286,082 | 8/1981 | Tsubakimoto et al. | 604/372 |
| 4,293,609 | 10/1981 | Erickson | 604/368 |
| 4,332,917 | 6/1982 | Heslinga | 525/207 |
| 4,338,417 | 7/1982 | Heslinga | 525/207 |
| 4,360,021 | 11/1982 | Stima | 604/368 |
| 4,408,010 | 10/1983 | Le-Khac | 525/73 |
| 4,420,588 | 12/1983 | Yoshioka | 525/184 |
| 4,443,492 | 4/1984 | Roller | 604/367 |
| 4,522,983 | 6/1985 | Le-Khac et al. | 525/316 |
| 4,610,678 | 9/1986 | Weisman et al. | 604/368 |
| 4,616,063 | 10/1987 | Le-Khac | 525/91 |
| 4,670,516 | 6/1987 | Sakmann et al. | 524/327.7 |
| 4,705,773 | 11/1987 | Le-Khac | 502/151 |
| 4,731,067 | 3/1988 | Le-Khac | 604/367 |
| 4,743,244 | 5/1988 | LeKhac | 604/376 |
| 4,749,746 | 6/1988 | Dean et al. | 525/73 |
| 4,777,231 | 10/1988 | Bailey et al. | 526/930 |
| 4,813,945 | 3/1989 | Le-Khac | 604/367 |

FOREIGN PATENT DOCUMENTS 0511193  1/1958  Canada ................... 524/108
190786  12/1977  Japan .

Primary Examiner—C. Fred Rosenbaum
Assistant Examiner—S. Rose
Attorney, Agent, or Firm—Dennis M. Kozak

[57] ABSTRACT

A copolymer of recurring units of at least one $\alpha,\beta$-unsaturated monomer and recurring units of at least one copolymerizable comonomer comprising, in its preferred embodiment from about 20 to about 80 percent pendant carboxylic acid units and from about 80 to about 20 percent pendant carboxylate salt units, is blended with a heterocyclic carbonate to produce a water-absorbing composition upon curing. The composition is particularly suitable for fiber formation.

20 Claims, No Drawings

ULTRAHIGH WATER-ABSORBING FIBER-FORMING COMPOSITION

This is a divisional of co-pending application Ser. No. 834,075 filed on Feb. 26, 1986, now abandoned.

This invention relates to water-absorbing compositions.

In one of its more specific aspects, this invention relates to the incorporation of water-absorbing compositions into articles of manufacture for the purpose of improving the absorbent properties of the articles.

Absorbent compositions are widely used in the manufacture of products which require high absorption capability. For example, water-absorbing compositions are used in the manufacture of surgical and dental sponges, tampons, sanitary napkins and pads, bandages, disposable diapers, meat trays, and household pet litter. Water-absorbing compositions are also used for the modification of soil to improve water retention and increase air capacity and for a host of other applications.

As used herein, the term "water" when used in the phrases "water-absorbing" and "water-absorbent" is understood to mean not only water but also electrolyte solutions such as body fluids.

A number of absorbent compositions have been developed which exhibit water absorption capacity. For example, U.S. Pat. Nos. 3,954,721 and 3,983,095 disclose preparations for derivatives of copolymers of maleic anhydride with at least one suitable vinyl monomer in fibrous form. The fibrous copolymers are rendered hydrophilic and water-swellable by reaction with ammonia or an alkali metal hydroxide. U.S. Pat. No. 3,810,468 discloses lightly cross-linked olefin-maleic anhydride copolymers prepared as substantially linear copolymers and then reacted with a diol or a diamine to introduce cross-linking. The resultant lightly cross-linked copolymers are treated with ammonia or an aqueous or alcohol solution of an alkali metal hydroxide. U.S. Pat. No. 3,989,586 describes the preparation of sorptive paper products by incorporating cross-linked copolymers of styrene or olefins with maleic anhydride in a paper web which is then treated to convert the copolymer to a water-swellable salt form. U.S. pat. No. 3,980,663 describes water-swellable absorbent articles made from carboxylic polyelectrolytes via cross-linking with glycerine diglycidyl ether. U.S. pat. Nos. 4,332,917 and 4,338,417 disclose blends of copolymers of styrene and maleic anhydride with polymers derived from a monomeric ester having vinyl unsaturation e.g., poly(vinyl acetate), cellulose triacetate cellulose aceto-butyrate, poly(ethyl-acrylate) and poly(methyl-methacrylate). U.S. Pat. No. 4,420,588 teaches a water absorbing rubber composition comprising a 1,3-diene rubber and a water-absorbing resin dispersed in the rubber.

The desirability of having water-absorbing compositions in fibrous forms is well known. For example, in sanitary products such as disposable diapers and tampons, fibers can be more easily confined within the product. In this respect, the prior art water-absorbing compositions are deficient; they do not facilitate fiber formation. Because of the speed of their crosslinking reactions, the prior art water-absorbing compositions possess no appreciable shelf life; fiber formation must be completed shortly after the compositions are prepared.

The water-absorbing compositions of this invention possess excellent shelf life. They facilitate fiber formation over a wide range of time and temperature. They also possess excellent integrity in the hydrogel or water-swollen state, exhibit excellent water and electrolyte solution absorption capacity, and are readily incorporated into conventional water-absorbing products using conventional methods.

According to this invention there is provided a composition which is water-absorbent upon curing comprising (a) a copolymer containing from about 25 to about 75 mole percent of at least one $\alpha,\beta$-unsaturated monomer bearing at least one pendant unit selected from the group consisting of carboxylic acid units and derivatives of carboxylic acid units and from about 75 to about 25 mole percent of at least one copolymerizable comonomer, wherein in said copolymer from about 20 to about 80 percent of the total pendant units introduced through the $\alpha,\beta$-unsaturated monomer are carboxylic acid units or must be converted into carboxylic acid units, and from about 80 to about 20 percent of the total pendant units are carboxylate metal salt units or must be converted into carboxylate salt units; and (b) a heterocylic carbonate.

According to this invention there is provided a method of producing a water-absorbing composition comprising the steps of: (a) preparing a blend of i) a copolymer containing from about 25 to about 75 mole percent recurring units of at least one $\alpha,\beta$-unsaturated monomer which bears at least one pendant unit selected from the group consisting of carboxylic acid units and derivatives of carboxylic acid units, and from about 75 to 25 mole percent recurring units of at least one copolymerizable comonomer, wherein in said copolymer from about 20 to about 80 mole percent of the total pendant units introduced through the recurring $\alpha,\beta$-unsaturated monomer units are carboxylic acid units or must be converted into carboxylic acid units and from about 80 to about 20 percent of the total pendant units are carboxylate salt units or must be converted into carboxylate salt units and ii) a heterocylic carbonate; and (b) curing the resulting blend.

According to this invention there is provided a method of absorbing water and electrolyte solutions comprising the step of contacting the water or electrolyte solution to be absorbed with a cured water absorbing composition comprising a blend of: (a) a copolymer containing from about 25 to about 75 mole percent of at least one $\alpha,\beta$-unsaturated monomer bearing at least one pendant unit selected from the group consisting of carboxylic acid units and derivatives of carboxylic acid units and from about 75 to 25 mole percent of at least one copolymerizable comonomer, wherein in said copolymer from about 20 to about 80 percent of the total pendant units introduced through the $\alpha,\beta$-unsaturated monomer are carboxylic acid units or must be converted into carboxylic acid units, and from about 80 to about 20 percent of the total pendant units are carboxylate salt units or must be converted into carboxylate salt units; and (b) a heteroxyclic carbonate.

An article of manufacture comprising a cured water-absorbing composition and a means for supporting said composition to present said composition for absorption usage, wherein said water-absorbing composition comprises a blend of: (a) a copolymer containing from about 25 to about 75 mole percent of at least $\alpha,\beta$-unsaturated monomer bearing at least one pendant unit selected from the group consisting of carboxylic acid units and derivatives of carboxylic acid units and from about 75 to about 25 mole percent of at least one copolymerizable comonomer, wherein in said copolymer from about 20 to 80 percent of the total pendant units introduced through the α,β-unsaturated monomer are carboxylic acid units or must be converted into carboxylic acid units, and from about 80 to about 20 percent of the total pendant units are carboxylate salt units or must be converted into carboxylate salt units; and (b) a heterocyclic carbonate.

According to this invention there is also provided a method of enhancing at least one water absorbing characteristic of an article which method comprises the step of incorporating into the article a cured water-absorbing composition comprising a blend of: (a) a copolymer containing from about 25 to about 75 mole percent of at least one α,β-unsaturated monomer bearing at least one pendant unit selected from the group consisting of carboxylic acid units and derivatives of carboxylic acid units and from about 75 to about 25 mole percent of at least one copolymerizable comonomer, wherein in said copolymer from about 20 to about 80 percent of the total pendant units introduced through the α,β-unsaturated monomer are carboxyl acid units or must be converted into carboxylic acid units, and from about 80 to about 20 percent of the total pendant units are carboxylate salt units or must be converted into carboxylate metal salt units; and (b) a heterocyclic carbonate, said composition being incorporated in the article in an effective amount to enhance at least one water-absorbing characteristic of the article as compared to the water-absorbing characteristics of the article in the absence of the composition.

Copolymers suitable for use to produce water-absorbing compositions of the invention will contain from about 25 to about 75 total mole percent recurring units of at least one α,β-unsaturated monomer and from about 75 to about 25 total mole percent recurring units of at least one copolymerizable comonomer. Preferably, the copolymer will contain from about 35 to about 65 total mole percent of recurring units of at least one α,β-unsaturated monomer and from about 65 to about 35 total mole percent of at least one copolymerizable comonomer. Most preferably, the copolymer will be an equimolar compolymer.

Suitable α,β-unsaturated monomers are those bearing at least one pendant carboxylic acid unit or derivative of a carboxylic acid unit. Derivatives of carboxylic acid units include carboxylic acid salt groups, carboxylic acid amide groups, carboxylic acid imide groups, carboxylic acid anhydride groups and carboxylic acid ester groups.

Suitable α,β-unsaturated monomers include maleic acid; crotonic acid; fumaric acid; mesaconic acid; the sodium salt of maleic acid; the sodium salt of 2-methyl, 2-butene dicarboxylic acid; the sodium salt of itaconic acid; maleamic acid; maleamide; N-phenyl maleimide; maleimide; maleic anhydride; fuameric anhydride; itaconic anhydride; citraconic anhydride; mesaconic anhydride; methyl itaconic anhydride; ethyl maleic anhydride; diethylmaleate; methylmaleate; and the like, and their mixtures.

Any suitable copolymerizable comonomer can be employed. Suitable copolymerizable comonomers include ethylene, propylene, isobutylene, C1 to C4 alkyl methacrylates, vinyl acetate, methyl vinyl ether, and styrenic compounds having the formula:

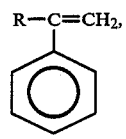

wherein R represents hydrogen or an alkyl group having from 1 to 6 carbon atoms and wherein the benzene ring may be substituted with low molecular weight alkyl or hydroxy groups.

Suitable $C_1$ to $C_4$ alkyl acrylates include methyl acrylate, ethyl acrylate, isopropyl acrylate, n-propyl acrylate, n-butyl acrylate, and the like, and their mixtures.

Suitable $C_1$ to $C_4$ alkyl methacrylates include methyl methacrylate, ethyl methacrylate, isopropyl methacrylate, n-propylmethymethacrylate, n-butyl methacrylate, and the like, and their mixtures.

And, suitable styrenic compounds include styrene, α-methylstyrene, p-methylstyrene, t-butyl styrene, and the like, and their mixtures.

The pendant units on the α,β-unsaturated monomer, will determine what, if any, additional reactions must be carried out to obtain a copolymer having the requisite pendant units necessary to produce the water-absorbing compositions of this invention, that is, about 20 to about 80 percent pendant carboxylic acid units and about 80 to about 20 percent pendant carboxylate salt units. Preferably, both units are present in an amount of from about 30 to about 70 percent.

In general, if the α,β-unsaturated monomer bears only carboxylic acid amide, carboxylic acid imide, carboxylic acid anhydride, carboxylic acid ester groups, or mixtures thereof, it will be necessary to convert at least a portion of such carboxylic acid derivative groups to carboxylic acid groups by, for example, a hydrolysis reaction. If the α,β-unsaturated monomer bears only carboxylic acid salt groups, acidification to form carboxylic acid groups will be necessary.

Similarly, the final copolymer must contain from about 80 to 20 percent pendant carboxylate salt units. Accordingly, it may be necessary to carry out a neutralization reaction. Neutralization of carboxylic acid groups with a strong organic or inorganic base such as NaOH, KOH, ammonia, ammonia-in-water solution, or organic amines will result in the formation of carboxylate salt units, preferably carboxylate metal salt units.

Moreover, the sequence and the number of reactions (hydrolysis, acidification, neutralization, etc.) carried out to obtain the desired functionality attached to copolymer backbone are not critical. Any number and sequence resulting in a final copolymer which possesses from about 20 to about 80 percent pendant carboxylic acid units and from about 80 to about 20 percent pendant carboxylate salt units is suitable.

One copolymer particularly suitable for use is a copolymer of maleic anhydride and isobutylene. Another is maleic anhydride and styrene. Suitable copolymers will have peak molecular weights of from about 5,000 to about 500,000 or more.

Suitable copolymers of maleic anhydride and isobutylene can be prepared using any suitable conventional method. Such copolymers are also commercially available from Kuraray Isoprene Chemical Company, Ltd., Tokyo, Japan, under the trademark ISOBAM. ISOBAM copolymers are available in several grades which are differentiated by viscosity molecular weight: ISO- BAM-10, 160,000 to 170,000; ISOBAM-06, 80,000 to 90,000; ISOBAM-04, 55,000 to 65,000; and ISOBAM-600 6,000 to 10,000.

To produce a water-absorbing composition of this invention, at least one copolymer and at least one heterocyclic carbonate are blended such that the water-absorbing composition contains in weight percent, from about 80 to about 99.5 total copolymer and from about 0.5 to about 20 heteracyclic carbonate. Preferably, the composition will contain from about 90 to about 99 weight percent total copolymer and from about 1 to about 10 weight percent total heterocyotic carbonate.

Any suitable heterocyclic carbonate can be employed Preferably the heterocyclic carbonates are those represented by the following general structure:

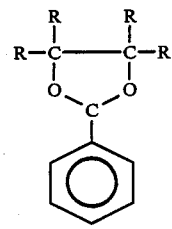

wherein each R separately represent a hydrogen atom, an alkyl group, an aromatic group, a halogen group, a substitute alkyl group, or a substituted aromatic group.

Heterocyclic carbonates represented by the above structure include propylene carbonate, ethylene carbonate, 1,2-butylene carbonate, 2,3-butylene carbonate, phenylethylene carbonate and the like, and their mixtures. Propylene carbonate is preferred.

The water-absorbing composition of this invention can be prepared using any suitable blending method such as described in the Examples which follow. After the water-absorbing composition is prepared, but typically before it is cured and in some instances as it is curing it is processed into any desired form using conventional methods of fabrication. For example, the water-absorbing composition can be subjected to casting; spray drying; air-assisted spray drying; air attenuation; wet, dry or flash spinning; and the like. The selection of the process is typically dictated by the shape or form needed for end use. Forms that the water-absorbing composition may be fabricated into include films or sheets, powders and granules, fibers and any form into which fibers can be processed such as for example milled fibers, chopped fibers, fluff or bulk fibers, strands, yarns, woven fabrics, nonwoven mats and the like using a variety of methods, including twisting, beaming, slashing, warping, quilling, severing, texturizing, weaving, knitting, braiding etc.

While not meaning to be limited to any theory, the heterocyclic carbonate is believed to serve as a high temperature, slow-reacting, cross-linking agent for the copolymer resulting in the formation of covalent cross-link bonds upon curing. For example, it has been found that, if a styrene-maleic anhydride copolymer is blended with propylene carbonate to form a water-absorbing composition according to this invention, a temperature about 150° C. or higher is typically required to cure. Similarly, if an ethylene-maleic anhydride copolymer is employed, a temperature of 140° C. or higher is typically needed to cure. And, if an isobutylene-maleic anhydride copolymer is employed, a temperature of 200° C. or higher is typically needed to cure.

Without meaning to limit the invention, the water-absorbing compositions of this invention are particularly well suited for being made into fibers because of the wide time and temperature ranges in which they can be shaped. More specifically, the water-absorbing compositions of this invention can be formulated to cure at temperatures within the range of from about 140° C to about 250° C. or higher and possess shelf lifes in excess of two months as demonstrated in Example 11. Hence, the water-absorbing compositions of this invention can be easily made into fibers using conventional methods and equipment.

The water-absorbing compositions of this invention and articles of manufacture into which the compositions are incorporated are suitable for use in a wide range of absorptive functions. In general, the articles into which the water-absorbing compositions are incorporated serve the function of supporting the composition and presenting it in a form adapted for absorptive end use. Means to support and present the composition for absorptive use include, but are not meant to be limited to bandages, surgical and dental sponges, tampons, sanitary napkins and pads, disposable diapers, meat trays, pads for absorption of perspiration, and the like.

In one embodiment, a water-absorbing composition of this invention is incorporated into a disposable diaper, using conventional fabrication methods to form a diaper composite having the following typical layers: (1) an outer (away from the body) of impermeable polyethylene film; (2) a first cellulosic pulp layer superimposed on the film; (3) a layer of a cured water-absorbing composition of this invention in the form of e.g. powder, fibers, flugg e.g. a fibrous mass, a non-woven fiber mat or a woven fabric; (4) an optional, second cellulosic pulp layer and (5) an inner permeable polyethylene film layer.

Fibers made from the water-absorbing compositions of this invention are particularly suitable for absorbent applications. It is well known that a mass of fibers provides a large surface area for contact with the liquid material to be absorbed and because fibers can be easily confined within the article into which they are incorporated.

The following examples serve to further demonstrate the invention.

EXAMPLE I

This example demonstrates the preparation of a copolymer of an $\alpha,\beta$-unsaturated monomer and a copolymerizable comonomer suitable for use in the practice of this invention.

A solution of about 240 g of maleic anhydride, about 255 g of styrene, and 2370 ml of methyl ethyl ketone was prepared and introduced into a one gallon stirred reactor at room temperature under a nitrogen atmosphere. Free radical polymerization was initiated by charging about 8.20 g of VAZO 65 polymerization initiator (azoisobutyronitrile E. I. DuPont) into the reactor. The polymerization reaction was conducted for about 24 hours at a temperature of about 55° C. Net, tetrahydrofuran was added to dilute the reactor contents. And the polymerization product, a copolymer of styrene and maleic anhydride, was recovered by precipitation into methanol with high speed stirring. The copolymer was dried overnight at 30° C in a vacuum oven, and then at 90° C for about one hour. About 499 g of copolymer were recovered.

The dried styrene-maleic anhydride copolymer was analyzed by titration of maleic acid and found to contain 43 mole percent maleic anhydride (41.7 wt.%). The balance of the copolymer was styrene. The copolymer was found to have a glass transition temperature of 234° C by differential scanning calorimetry and a peak molecular weight of 108,000 by gel permeation chromatography using polystyrene standards.

EXAMPLE 2

This example demonstrates the preparation of five water-absorbing compositions of the invention using the styrene-maleic anhydride copolymer of Example 1. A series of five water-absorbing compositions (I through V) was prepared. Each composition was individually prepared as follows.

About 10 g of the copolymer and about 150 g of demineralized water were added to a mixing vessel with agitation and the vessel contents were heated to about 90° C. At a temperature of about 90° C a solution of a predetermined amount of sodium hydroxide (98.9% purity, pellets) in 10 g of dimineralized water was slowly added to the mixing vessel over a one hour period with agitation. The amount of sodium hydroxide added to each composition was calculated to convert, here, neutralize, a certain percentage of the pendant carboxylic acid units (which were converted from acid anhydride units) into carboxylate sodium salt units. After the addition was completed, agitation was continued for about one hour and the copolymer dissolved into the solution.

The resulting copolymer-containing solution was cooled to room temperature and 0.5 g of propylene carbonate (99% purity, Aldrich Chemical) was added to the solution with agitation. The resulting composition was poured onto Mylar film.

The composition on the Mylar film was allowed to air dry and then further dried in a vacuum oven for 30 minutes at 60° C. The composition was ground into particles having diameters of about 300 microns and cured at 160° C. for about 30 minutes in a hot air circulation oven.

Using the above-described procedure, five water-absorbing compositions (I-V) were prepared, employing the amounts of sodium hydroxide set forth in following table. Moreover, each composition, was subjected to testing to determine its Swell Index, Percent Solubility, and the results are also shown in the Table. The test procedures used to determine Swell Index and Percent Solubility are described below.

| Composition | I | II | III | IV | V |
| --- | --- | --- | --- | --- | --- |
| Amount of NaOH added (g) | 1.27 | 1.7 | 1.98 | 2.13 | 3.4 |
| % Pendant carboxylate Metal Salt Units | 37 | 50 | 58 | 63 | 100 |
| Swell Index | | | | | |
| @ Atm. Pressure | 17.8 | 41.9 | 53.8 | 49.7 | Soluble |
| @ 0.5 psi | 13.4 | 29.6 | 41.8 | 39.3 | Soluble |

Swell Index

This test procedure is described in U.S. Pat. No. 4,454,055 the teachings of which are incorporated herein by reference thereto. The test procedure and equipment used herein were modified slightly as compared to the procedure and equipment described in U.S. Pat. No. 4,454,055.

To determine the Swell Index at atmospheric (room) pressure, about 0.2 to 0.3 g of the water-absorbing composition to be tested is placed in an empty W-shaped tea bag. The tea bag containing the composition is immersed in brine (0.9 wt.% NaCl) for 10 minutes, removed and allowed o sit on a paper towel for 30 seconds to remove surface brine. The Swell Index of the composition, that is, the units of liquid absorbed per each unit of sample is calculated using the following formula:

$$\text{Swell Index} = \frac{\text{Weight of Wet Composition}}{\text{Weight of Dry Composition}} - 1$$

To determine Swell Index under pressure, the following modified procedure was used.

After the tea bag containing the sample composition is immersed in brine and surface brine is removed, it is immediately placed in a 16 cm ID Buchner funnel fitted with a 2000 ml sidearm vacuum filter flask and connected to a manometer. Then, a piece of dental dam rubber sheeting is securely fixed over the mouth of the funnel such that the sheeting just rests on the tea bag. Next, a vacuum sufficient to create the desired pressure is drawn on the flask for a period of five minutes, and, the Swell Index under pressure is calculated using the above formula.

Percent Solubility

About 0.5 g of the water-absorbing composition sample to be tested is dispersed in about 150 g of brine (0.9 wt.% NaCl) at room temperature for 20 minutes with occasional gentle agitation. After 20 minutes, the mixture is filtered through a 150 micron polypropylene screen. Next, the filtrate is dried to a constant weight in an oven and the weight of soluble composition determined by subtracting the weight of the NaCl from the total weight of the dry filtrate. Percent solubility is then determined using the following formula:

$$\text{Percent Solubility} = \frac{\text{Weight of Soluble Composition}}{\text{Weight of Sample Composition}} \times 100$$

EXAMPLE 3

This example demonstrates the preparation of a water-absorbing composition of this invention using substantially the procedure of Example 2 and further illustrates the effect of different cure temperatures on its absorbent properties.

Using substantially the procedure described in Example 2, about 10 g of the styrene-maleic anhydride copolymer produced in Example 1 were hydrolyzed and then partially neutralized with 1.7 g, of sodium hydroxide to convert about 50% of the pendant carboxylic acid units on the copolymer to carboyxlate sodium salt units. Next, the resulting composition (VI) was blended with 10 phr (9.1 wt.%) of propylene carbonate and, the composition was divided into thirds. Each third was cured for thirty minutes at a different cure temperature. One was cured at 150° C; one at 160° C. and the other at 170° C. The results were as follows:

| Composition | VI | VI | VI |
| --- | --- | --- | --- |
| Cure Temp. (°C.) | 150 | 160 | 170 |

-continued

| Composition | VI | VI | VI |
|---|---|---|---|
| Swell Index | | | |
| @ Atm. Pressure | 37.5 | 23.1 | 16.5 |
| @ 0.5 psi | 28 | 16.9 | 12.7 |
| % Solubility | 12.8 | 8.3 | 6.4 |

EXAMPLE 4

This example demonstrates the preparation of two water-absorbing compositions of the invention using substantially the procedure of Example 2, as herein described. Data illustrative of the effect of heterocyclic carbonate content on absorbent properties are also presented below.

Using substantially the procedure of Example 2, Composition II, three compositions (VII and VIII, and a Control) were prepared. All compositions were hydrolyzed and partially neutralized with NaOH to convert about 50% of the pendant carboxylic acid units to carboxylate sodium salt units.

Composition VII differed from Composition II in that it was prepared by blending the styrene-maleic anhydride copolymer with 10 phr of propylene carbonate.

Composition VIII differed in that it was prepared by blending the copolymer with 15 phr of propylene carbonate No propylene carbonate was added to the Control composition.

The results of the effect of propylene carbonate content on absorbent properties of these compositions are set forth below. The absorbent properties of Composition II are listed for comparative purposes; it employed 5 phr of propylene carbonate.

| Composition | Control | II | VII | VIII |
|---|---|---|---|---|
| Propylene Carbonate (phr) | 0 | 5 | 10 | 15 |
| Swell Index: | | | | |
| @ Atm. Pressure | Soluble | 41.9 | 23.1 | 24.4 |
| @ 0.5 psi | Soluble | 29.6 | 16.9 | 16.8 |
| % Solubility | 100 | 12.8 | 8.3 | 9.8 |

EXAMPLE 5

This example demonstrates the preparation of a water-absorbing composition of this invention using an equimolar, alternating copolymer of ethylene-maleic anhydride designated EMA-31 (100,000 molecular wt.), commercially available from Monsanto.

About 15 g of EMA-31 copolymer, 150 g of demineralized water and 0.6 g (4 phr) of propylene carbonate were added to a mixing vessel with agitation and heated to about 90° C. When the contents of the vessel reached about 90° C., about 4.85 g of NaOH dissolved in 20 ml water were slowly introduced over a 30 minute period.

After the NaOH addition was completed, the contents of the mixing vessel were agitated for about 30 minutes after which the EMA-31 copolymer was observed to be completely dissolved. The pH of the resulting solution was about 6.

Water in the resulting solution was allowed to evaporate until a solid composition was obtained and the solid composition was further dried in a vacuum oven at 50° C for 2 hours. Next, the composition was ground into a powder having particle diameters of about 300 microns and the powder was cured at 160° C for 30 minutes in a hot air circulation oven.

The absorbent properties of the resulting water-absorbing. Composition IX, are shown in the following table.

| Composition | IX |
|---|---|
| % Pendant Carboxylate Salt Units | 50 |
| Swell Index: | |
| @ Atm. Pressure | 25.7 |
| @ 0.1 psi | 22.7 |
| @ 0.5 psi | 18.3 |
| @ 1.5 psi | 16.9 |
| % Solubility | 9.6 |

EXAMPLE 6

This example demonstrates the preparation of two water-absorbing compositions of this invention (Compositions X and XI) using substantially the procedure of Example 5, as herein described.

Composition X differed from the procedure and materials of Example 5 in that the EMA-31 copolymer was blended with one phr of ethylene carbonate.

Composition XI differed from the procedure and materials of Example 5 in that the EMA-31 copolymer was blended with one phr of ethylene carbonate and cured at 150° C.

The absorbent properties of Compositions X and XI were as follows:

| Composition | X | XI |
|---|---|---|
| Ethylene Carbonate (phr) | 1 | 1 |
| Cure Temperature (°C.) | 160 | 150 |
| Swell Index: | | |
| @ Atm. Pressure | 31.3 | 37.6 |
| @ 0.1 psi | 30.4 | 34.3 |
| @ 0.5 psi | 26.1 | 28.7 |
| @ 1.5 psi | 21.9 | 24.6 |
| % Solubility | 14.2 | 15.1 |

EXAMPLE 7

This example demonstrates the preparation of a water-absorbing composition of this invention, Composition XII, using ISOBAM 10, an isobutylene/maleic anhydride copolymer commercial available from Kuraray Isoprene Chemical Company, Ltd. ISOBAM 10, has a molecular weight of 170,000, and a maleic anhydride content of about 59.3 wt.% (46.6 mole %) as determined by titration of maleic acid.

About 957 g of the isobutylene-maleic anhydride copolymer, and about 1740 g of demineralized water were charged to a one gallon stirred reactor and heated to about 90° C. A solution of 248 g of NaOH dissolved in about 372 g of water was added slowly to the reactor over a 45 minute period. Next, 47.8 g (5 phr) of propylene carbonate were introduced into the reactor and the reactor contents were stirred for about 10 hour to dissolve the isobutylene-maleic anhydride copolymer. The pH of the resulting solution was 6.5. The neutralization reaction resulted in about 53.5% of the pendant units on the 46.6 mole % recurring units of maleic anhydride being converted carboxylate sodium salt units.

The resulting solution was allowed to cool to room temperature and then atenuated into fibers by forcing the solution through an orifice into a current of warm air and wrapping the resulting attenuated fibers onto a Mylar film covered drum. The resulting fibers had diameters of about 10 microns. Two fibrous mass samples of the fibers produced from the resulting Composition XII were separately cured for 30 minutes at 210° C. and at 220° C.

The following table illustrates the absorbent properties of Composition XII in fiber form.

| Composition (fibers) | XII | XII |
|---|---|---|
| Cure Temperature (°C.) | 210 | 220 |
| Swell Index: | | |
| @ Atm. Pressure | 36.3 | 33.4 |
| @ 0.5 psi | 26.0 | 21.8 |
| % Solubility | 17.7 | 15.5 |

EXAMPLE 8

This example demonstrates the preparation of four water-absorbing compositions of this invention (Compositions XIII–XVI) using substantially the materials and procedure of Example 7.

Each composition was prepared using an isobutylene-maleic anhydride copolymer (ISOBAM 10) which had been treated to covert 53.5% of the pendant units, introduced into the copolymer through the 46.6 mole % recurring units of maleic anhydride, to carboxylate salt units.

All four compositions were ground into power and the powers were separately cured and their absorbent properties tested.

The absorbent property data obtained for the four compositions prepared in accordance with the listed composition and procedure data are shown in the following table.

| Composition | XIII | XIV | XV | XVI |
|---|---|---|---|---|
| Propylene Carbonate (phr) | 0 | 0 | 0 | 1 |
| Ethylene Carbonate (phr) | 1 | 2 | 5 | 1 |
| Cure Temperature (°C.) | 210 | 210 | 210 | 210 |
| Cure Time (min) | 30 | 30 | 30 | 30 |
| Swell Index | | | | |
| @ Atm. Pressure | 66.5 | 51.8 | 31.4 | 58.5 |
| @ 0.1 psi | 59.7 | 43.6 | 31.1 | 58.6 |
| @ 0.5 psi | 53.0 | 39.5 | 24.3 | 50.0 |
| @ 1.5 psi | 48.0 | 37.8 | 22.1 | 47.5 |
| % Solubility | 19.8 | 12.3 | 11.3 | 16.5 |

EXAMPLE 9

This example demonstrates that the water-absorbing compositions of this invention possess excellent integrity in the hydrogel state.

A sample of Composition II, (taken before curing) was cured at 180° C for 30 minutes. Next, a 2.2885 g. sample of the cured composition was subjected to Soxhlet extraction using 500 ml of distilled water. The extraction was run at refluxing temperature for about 6 hours. The extracted polymer gel was recovered by drying in a vacuum oven at 100° C for 20 hours. The extracted, dried composition weighed 2.1147g.

The amount of soluble product found was 0.1738 g or 7.6 wt. %. No propylene carbonate residue was found in the extracted solution.

The results of Swell Index testing done on the extracted composition were as follows:

| | Extracted Composition |
|---|---|
| Swell Index: | |
| @ Atm. Pressure | 37.4 |
| @ 0.1 psi | 33.6 |
| @ 0.5 psi | 23.6 |
| @ 1.5 psi | 26.2 |

The above data indicate that the water-absorbing compositions of this invention possesses excellent absorbent properties after Soxhlet extraction. Moreover, the test results indicate that the water-absorbing compositions are crosslinked through covalent bonds.

EXAMPLE 10

This example demonstrates the preparation of fibers of different diameters from the water-absorbing composition of Example 7 —Composition XII.

Fibers of four different diameters 6, 75, 110, and 190 microns, were prepared by air attenuation of a liquid stream of Composition XII (before curing) using a spray nozzle assembly of the type commercially available from Spraying Systems Company, Wheaton, Ill., modified to be conical at the tip to reduce turbulent air flow.

After the fibers having different diameters were formed, they were separately cured at 210° C for 30 minutes and then the fibers were tested for absorbency. The test results are shown below.

| Composition | XII | XII | XII | XII |
|---|---|---|---|---|
| Fiber diameter (microns) | 6 | 75 | 110 | 190 |
| Swell Index: | | | | |
| @ Atmospheric Pressure | 34.1 | 52.4 | 69.5 | 65.2 |
| @ 0.5 psi | 28.0 | 36.6 | 51.8 | 56.8 |
| % Solubility | 18.1 | 12.4 | 14.7 | 11.8 |

The above data illustrate that fibers produced from a water-absorbing composition of this invention have been found to be capable of absorbing up to 69.5 times their weight.

EXAMPLE 11

This example demonstrates that the water-absorbing compositions of this invention possess excellent shelf life when in solution form.

Two samples of the solution used to produce Composition XII were aged. One sample was aged for one month at ambient temperature and then for 2 days at 100° C. The other sample was aged for two months at ambient temperature. After aging, fibers were prepared from the solutions and the resulting fibers were cured for 30 minutes at 210° C.

The absorbent property data of the fibers produced after aging are compared with the absorbent property data of the fibers produced in Example 7, in the absence of aging.

| Composition | XII | XII | XII |
|---|---|---|---|
| Time of Solution Aging | 0 | 1 mo. | 2 mo. |
| Swell Index: | | | |
| @ Atmospheric Pressure | 36.3 | 37.2 | 38.0 |
| @ 0.1 psi | 30.0 | 30.8 | 29.9 |
| @ 0.5 psi | 26.0 | 26.6 | 24.9 |
| @ 1.5 psi | 23.6 | 24.1 | 21.2 |
| % Solubility | 17.7 | 16.4 | 18.6 |

The above data illustrate that, even after aging a water-absorbing composition of this invention for two months and then forming fibers, the fibers showed no appreciable change in their Swell Index values, hence indicating no appreciable loss in absorption properties.

It will be evident from the foregoing that various modifications can be made to this invention. Such, however, are considered as being within the scope of the invention.

What is claimed is:

1. A stable, heat curable, aqueous composition comprising in weight percent:
   (a) from about 80 to about 99.5 of a copolymer containing from about 25 to about 75 mole percent of about 20 to about 80 percent neutralized carboxylic acid substituted ethylenic units and from about 75 to about 25 mole percent recurring units of at least one copolymerizable comonomer; and
   (b) at least one heterocyclic carbonate compound wherein the resulting aqueous composition is uncured and stable at room temperature.

2. A method of rendering the aqueous composition of claim 1 water-absorbing which comprises heating the composition to a temperature sufficient to cure.

3. A method of absorbing water and electrolyte solutions which comprises contacting the water of electrolyte solution to be absorbed wit the cured composition of claim 1.

4. A method of producing a water-absorbing composition comprising the steps of:
   (a) preparing a blend of (i) from about 80 to about 99.5 of a copolymer containing from about 25 to about 75 mole percent recurring units of at least one $\alpha,\beta$-unsaturated monomer bearing at least one pendant unit selected from the group consisting of carboxylic acid units and derivatives of carboxylic acid units and from about 75 to about 25 mole percent recurring units of at least one copolymerizable comonomer, wherein in said copolymer from about 20 to about 80 percent of the total pendant units introduced through the recurring units of the $\alpha,\beta$-unsaturated monomer must either be carboxylic acid units or must be converted into carboxylic acid units and from about 80 to about 20 percent of the total pendant units must either be carboxylate salt units or must be converted into carboxylate metal salt units; and (ii) from about 0.5 to about 20 weight percent of a heterocyclic carbonate; and
   (b) curing the resulting blend.

5. The method of claim 4 comprising the step of forming the blend into a shaped article the blend is prepared but before it is fully cured.

6. The method of claim 5 in which the blend is formed into fibers.

7. The method of claim 5 in which the blend is formed into a powder.

8. The method of claim 5 in which the blend is formed into a film.

9. The method of claim 4 in which said curing is induced by heating the blend.

10. A stable, heat curable, aqueous composition which is water-absorbent upon curing comprising in weight percent:
    (a) from about 80 to about 99.5 of a copolymer containing from about 25 to about 75 mole percent recurring units of at least one $\alpha,\beta$-unsaturated monomer bearing at least one pendant unit selected from the group consisting of carboxylic acid units and derivatives of carboxylic acid units and from about 75 to about 25 mole percent mole percent recurring units of at least one copolymerizable comonomer, wherein in said copolymer from about 20 to about 80 percent of the total pendant units introduced through the recurring units of the $\alpha,\beta$-unsaturated monomer must either be carboxylic acid units or must be converted into carboxylic acid units, and from about 80 to about 20 percent of the total pendant units must either be carboxylic salt units or must be converted into carboxylate salt units; and
    (b) from about 0.5 to about 20 of a heterocyclic carbonate, wherein the resulting aqueous composition is uncured and stable at room temperature.

11. The composition of claim 10 in which said copolymer contains from about 35 to about 65 mole percent recurring units of said at least one $\alpha,\beta$-unsaturated monomer and from about 65 to about 35 mole percent of said at least one copolymerizable comonomer.

12. The composition of claim 10 in which said copolymer is an equimolar copolymer.

13. The composition of claim 10 comprising in weight percent from about 90 to about 99 of said copolymer and from about 1 to about 10 of said heterocyclic carbonate.

14. The composition of claim 10 in which said copolymer is a copolymer of styrene and maleic anhydride.

15. The composition of claim 10 in which said copolymer is a copolymer of ethylene and maleic anhydride.

16. The composition of claim 10 in which said copolymer is a copolymer of isobutylene and maleic anhydride.

17. The composition of claim 10 in which said heterocyclic carbonate is propylene carbonate.

18. The composition of claim 10 in which said heterocyclic carbonate is ethylene carbonate.

19. A method of absorbing water and electrolyte solutions which comprises contacting the water or electrolyte solution to be absorbed with the cured composition of claim 10.

20. The aqueous composition of claim 10 in being heat curable at a temperature of about 140° C. or higher.

* * * * *